(12) United States Patent
Nishii

(10) Patent No.: US 11,032,469 B2
(45) Date of Patent: Jun. 8, 2021

(54) IMAGING CONTROL APPARATUS, RADIATION IMAGING SYSTEM, IMAGING CONTROL METHOD, AND STORAGE MEDIUM

(71) Applicant: CANON KABUSHIKI KAISHA, Tokyo (JP)

(72) Inventor: Yuichi Nishii, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 112 days.

(21) Appl. No.: 16/407,278

(22) Filed: May 9, 2019

(65) Prior Publication Data

US 2019/0356846 A1 Nov. 21, 2019

(30) Foreign Application Priority Data

May 15, 2018 (JP) .............................. JP2018-093978

(51) Int. Cl.
*H04N 5/232* (2006.01)
*A61B 6/00* (2006.01)
*H04N 5/32* (2006.01)

(52) U.S. Cl.
CPC ......... *H04N 5/23229* (2013.01); *A61B 6/461* (2013.01); *A61B 6/542* (2013.01); *H04N 5/32* (2013.01); *A61B 6/545* (2013.01)

(58) Field of Classification Search
CPC ......... A61B 6/461; A61B 6/542; A61B 6/545; H04N 5/23229; H04N 5/32
See application file for complete search history.

(56) References Cited

U.S. PATENT DOCUMENTS

| 6,422,751 | B1 | 7/2002 | Aufrichtig et al. |
| 8,724,772 | B2 | 5/2014 | Nishii |
| 9,031,194 | B2 | 5/2015 | Nishii |
| 9,538,969 | B2 | 1/2017 | Nishii et al. |
| 10,188,364 | B2 | 1/2019 | Nishii |
| 2011/0052016 | A1 | 3/2011 | Nishii |
| 2012/0243663 | A1 | 9/2012 | Nishii |
| 2017/0251989 | A1 | 9/2017 | Nishii |
| 2017/0265837 | A1 | 9/2017 | Suzuki et al. |
| 2019/0328350 | A1* | 10/2019 | Niibe ................ G06T 7/0012 |

FOREIGN PATENT DOCUMENTS

JP 3133741 2/2001

* cited by examiner

*Primary Examiner* — Mark R Gaworecki
(74) *Attorney, Agent, or Firm* — Venable LLP

(57) ABSTRACT

An imaging control apparatus comprising: an irradiation field obtaining unit configured to obtain irradiation field information in radiation imaging by an irradiation field obtaining method based on any one of a radiation image obtained by the radiation imaging, imaging information concerning the radiation imaging, and preset irradiation field information in the radiation imaging; and an area dose obtaining unit configured to obtain an area dose in the radiation imaging based on the irradiation field information. In a case the irradiation field information is not obtained, the irradiation field obtaining unit obtains the irradiation field information based on an irradiation field obtaining method different from the irradiation field obtaining method.

25 Claims, 12 Drawing Sheets

IMAGING CONTROL APPARATUS, RADIATION IMAGING SYSTEM, IMAGING CONTROL METHOD, AND STORAGE MEDIUM

BACKGROUND OF THE INVENTION

Field of the Invention

The present invention relates to an imaging control apparatus, a radiation imaging system, an imaging control method, and a storage medium.

Description of the Related Art

In recent years, with recognition of importance on radiation exposure dose management for subjects, area doses are required to be displayed. Mounting an area dosimeter on a system allows measurement of area doses. However, in order to suppress an increase in cost due to the mounting of an area dosimeter or for a radiation imaging system on which an area dosimeter is difficult to mount, radiation imaging systems that can calculate radiation doses without mounting any area dosimeters have been proposed. Japanese Patent No. 3133741 discloses an arrangement using a simplified dose conversion method such as an NDD (Non Dosimeter Dosimetry) method to calculate area doses.

Assume that area doses are obtained by using a simplified dose conversion method such as an NDD method. In this case, in a case a collimator is adjusted at the time of imaging, it is sometimes not possible to obtain, in real time, information about a region irradiated with radiation (to be referred to as an "irradiation field" hereinafter) from a radiation generating apparatus, that is, collimator information. This causes a failure to obtain an area dose corresponding to executed radiation imaging.

SUMMARY OF THE INVENTION

The present invention provides a technique that can obtain an area dose based on irradiation field information concerning executed radiation imaging.

According to one aspect of the present invention, there is provided an imaging control apparatus comprising: an irradiation field obtaining unit configured to obtain irradiation field information in radiation imaging by an irradiation field obtaining method based on any one of a radiation image obtained by the radiation imaging, imaging information concerning the radiation imaging, and preset irradiation field information in the radiation imaging; and an area dose obtaining unit configured to obtain an area dose in the radiation imaging based on the irradiation field information, wherein in a case the irradiation field information is not obtained, the irradiation field obtaining unit obtains the irradiation field information based on an irradiation field obtaining method different from the irradiation field obtaining method.

According to the present invention, an area dose can be obtained based on irradiation field information in executed radiation imaging.

Further features of the present invention will become apparent from the following description of exemplary embodiments (with reference to the attached drawings).

DESCRIPTION OF THE EMBODIMENTS

Embodiments of the present invention will be exemplarily described below in detail with reference to the accompanying drawings. Note, however, the constituent elements described in the embodiments are merely examples, and are not limited by each embodiment described below. Radiation includes $\alpha$-rays, $\beta$-rays, $\gamma$-ray, and various types particle rays in addition to X-rays.

First Embodiment

Figure 1:
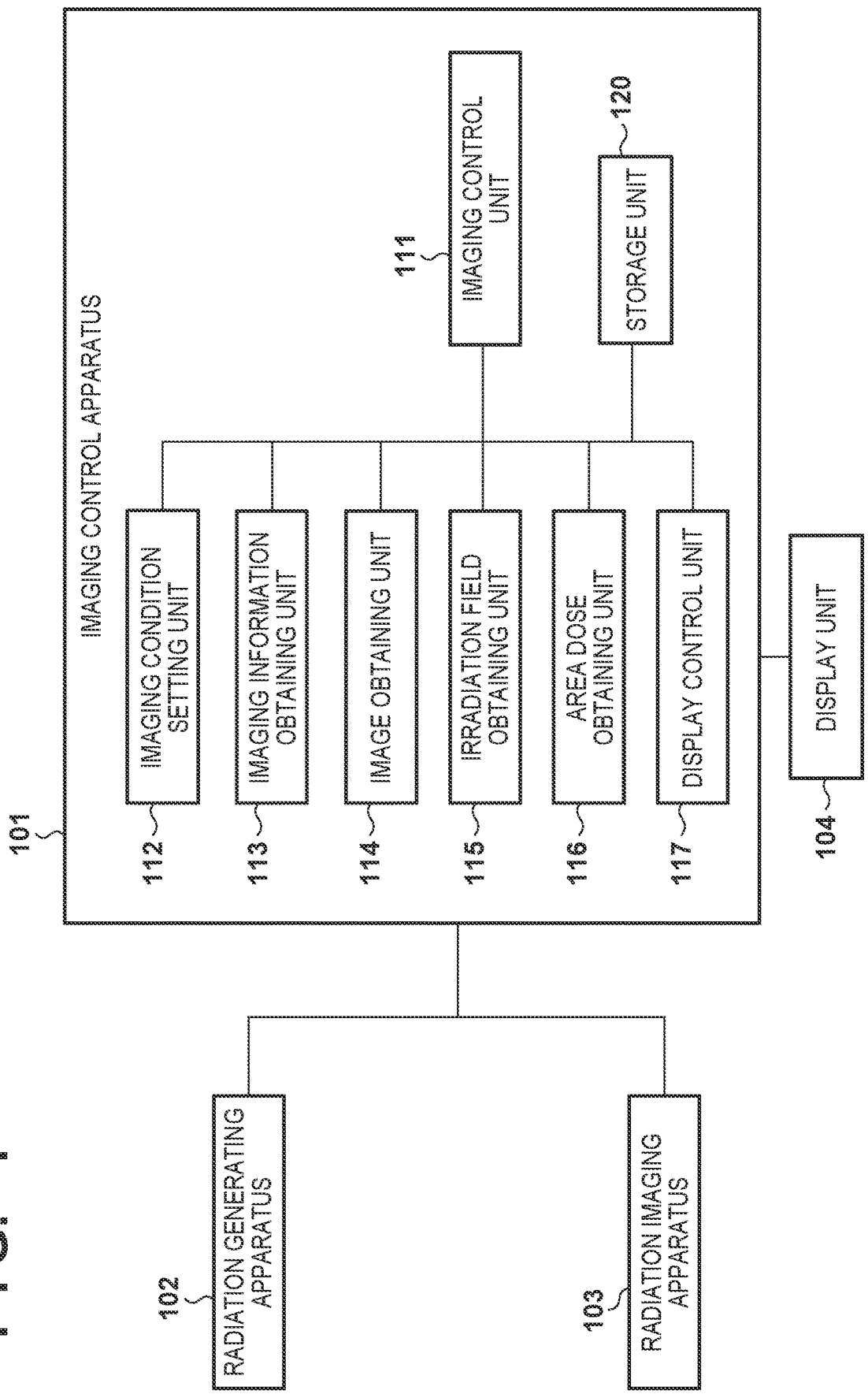
FIG. 1 is a block diagram exemplarily showing the arrangement of a radiation imaging system according to the first embodiment.

FIG. 1 exemplarily shows the arrangement of a radiation imaging system according to the first embodiment. The radiation imaging system includes an imaging control apparatus 101 that controls a radiation generating apparatus 102 and a radiation imaging apparatus 103. The imaging control apparatus 101 controls radiation imaging by communicating with the radiation generating apparatus 102 and the radiation imaging apparatus 103 (radiation detector). The radiation imaging apparatus 103 makes transition to an imaging ready state in accordance with an instruction from the imaging control apparatus 101, and performs radiation imaging in synchronism with the radiation generating apparatus 102.

The radiation generating apparatus 102 applies radiation based on imaging conditions. A subject is irradiated with radiation applied from the radiation generating apparatus 102. The radiation imaging apparatus 103 detects radiation applied from the radiation generating apparatus 102, and outputs radiation image data. That is, the radiation imaging apparatus 103 detects radiation that is applied from the radiation generating apparatus 102 and enters after being transmitted through a subject, and generates radiation image data.

The imaging control apparatus 101 includes, as functional components, an imaging control unit 111, an imaging condition setting unit 112, an imaging information obtaining unit 113, an image obtaining unit 114, an irradiation field obtaining unit 115, an area dose obtaining unit 116, and a display control unit 117.

The imaging control unit 111 can control the operations of the respective units of the imaging control apparatus 101 as functional components, that is, the imaging condition setting unit 112, the imaging information obtaining unit 113, the image obtaining unit 114, the irradiation field obtaining unit 115, the area dose obtaining unit 116, and the display control unit 117 as well as performing overall operation control of the imaging control apparatus 101.

The imaging condition setting unit 112 performs presetting associated with imaging conditions such as a tube voltage, tube current, and irradiation time used for imaging with respect to the radiation generating apparatus 102 and the radiation imaging apparatus 103.

The imaging information obtaining unit 113 can obtain imaging information in actual radiation imaging from the radiation generating apparatus 102. For example, the imaging information obtaining unit 113 obtains imaging information in radiation imaging (a tube voltage, tube current, irradiation time, mAs value, and distance between the radiation generating apparatus 102 and a subject (SOD (Source-to-Object Distance)) from information held in the radiation generating apparatus 102 and the imaging control apparatus 101. Note that as imaging information, SID (Source-to-Image Distance) that is the distance between the radiation generating apparatus 102 and the detection surface of the radiation imaging apparatus 103 (radiation detector) may be used in addition to SOD.

The image obtaining unit 114 obtains a radiation image by radiation imaging based on radiation applied from the radiation generating apparatus 102. That is, the image obtaining unit 114 obtains the radiation image data generated by the radiation imaging apparatus 103 from radiation imaging apparatus 103.

The irradiation field obtaining unit 115 obtains irradiation field information in radiation imaging by an irradiation field obtaining method based on at least one of the radiation image obtained by radiation imaging, imaging information associated with radiation imaging, and preset irradiation field information concerning radiation imaging. In a case no irradiation field information can be obtained, the irradiation field obtaining unit 115 can obtain irradiation field information based on an irradiation field obtaining method different from the above irradiation field obtaining method.

The area dose obtaining unit 116 obtains an area dose in radiation imaging based on irradiation field information. That is, the area dose obtaining unit 116 obtains the area of an irradiation field based on information concerning the irradiation field obtained by the irradiation field obtaining unit 115. The area dose obtaining unit 116 then obtains an area dose based on the imaging information obtained by the imaging information obtaining unit 113 by using a simplified dose obtaining method such as an NDD method.

In the simplified dose obtaining method, for example, a dose information table is generated by measuring irradiation doses in advance, which associates imaging information in radiation imaging or preset imaging conditions for radiation imaging, such as tube voltages and tube currents, with irradiation doses in radiation imaging. This dose information table is stored in, for example, a storage unit 120 provided in the imaging control apparatus 101. The area dose obtaining unit 116 obtains information concerning an irradiation dose corresponding to imaging information by referring to the dose information table stored in the storage unit 120 when obtaining an irradiation dose. The area dose obtaining unit 116 obtains a corresponding irradiation dose based on imaging information from the dose information table, and obtains an area dose based on the obtained irradiation dose and the area of the irradiation field obtained from the irradiation field information.

The area dose obtaining unit 116 can obtain an irradiation dose at the detection position of a subject based on imaging information and the distance between the subject (detection position) and the radiation generating apparatus 102 by using, for example, an NDD method. If the detection position of a radiation dose is the position of a subject, it is possible to use an SOD that is the distance between the radiation generating apparatus 102 and the subject. If the detection position of a radiation dose is the position of the detection surface of the radiation imaging apparatus 103 (radiation detector), it is possible to use an SID that is the distance between the radiation generating apparatus 102 and the detection surface of the radiation imaging apparatus 103.

The area dose obtaining unit 116 obtains an irradiation dose on a subject (detection position) based on imaging information at the time of actual irradiation of the subject with radiation and the distance between the radiation generating apparatus 102 and the subject. The area dose obtaining unit 116 obtains an area dose based on the area of an irradiation field and the acquired irradiation dose. For example, an area dose can be obtained by multiplying the obtained irradiation dose by the area of the irradiation field.

The display control unit 117 performs display control to cause a display unit 104 to display the area dose obtained by the area dose obtaining unit 116.

(Image Processing or Processing Using Preset Irradiation Field Information)

Figure 2:
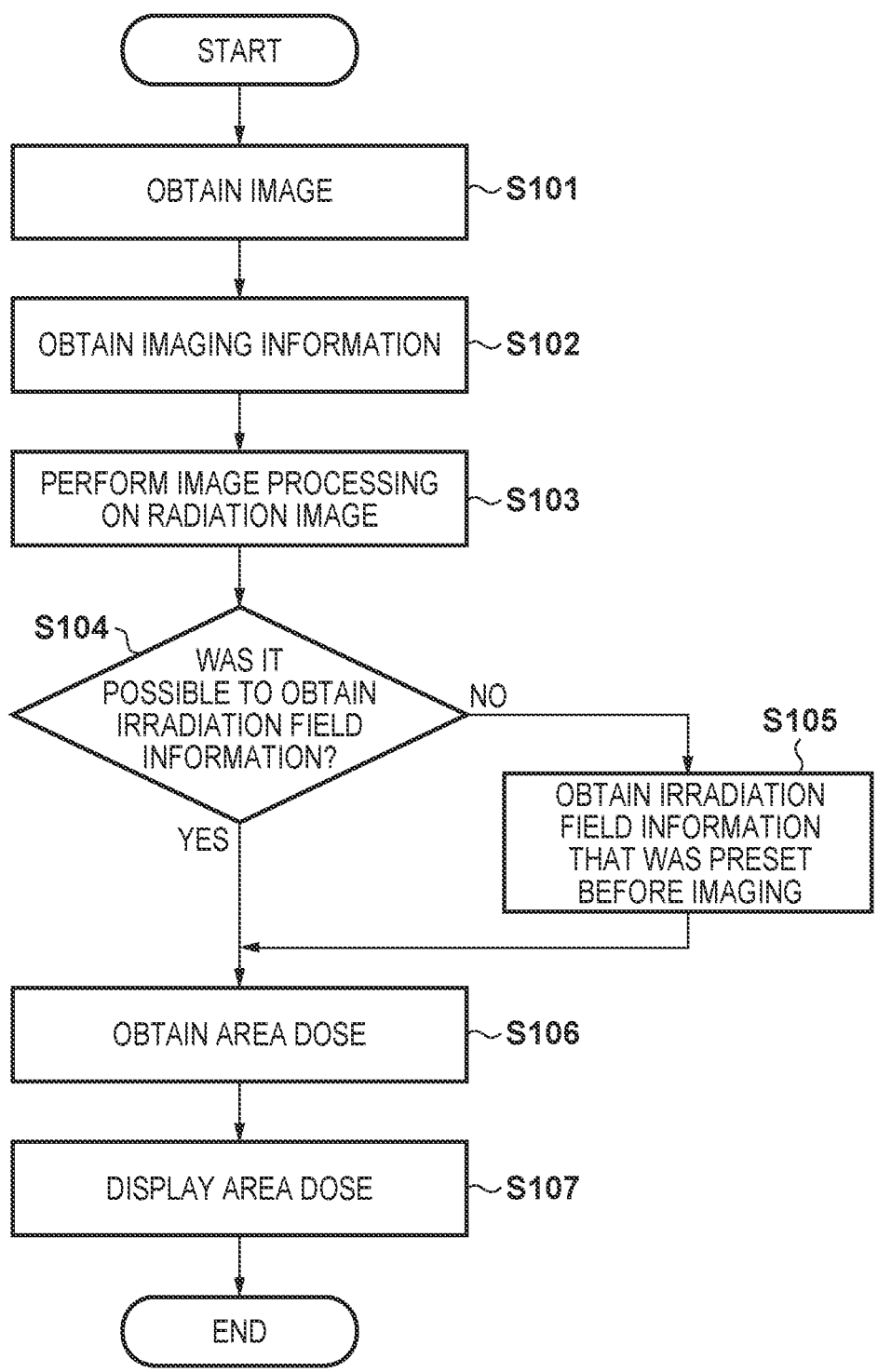
FIG. 2 is a flowchart for explaining a procedure for processing according to the first embodiment.

FIG. 2 explains a procedure for processing according to the first embodiment, and is a flowchart for explaining a procedure for the processing of obtaining an area dose and displaying the obtained area dose. This embodiment is described based on an example using an NDD method as a simplified dose obtaining method. However, the embodiment can use another dose obtaining method.

Referring to the flowchart of FIG. 2, the irradiation field obtaining unit 115 performs image processing for a radiation image as a first irradiation field obtaining method (step S103). If no irradiation field information can be obtained by image processing, irradiation field information in radiation imaging is obtained based on information included in imaging conditions (irradiation field information in radiation imaging which is preset as imaging conditions) as a second irradiation field obtaining method (step S105). In a case preset irradiation field information is included as information included in imaging conditions for radiation imaging, that is, in a case preset irradiation field information is included in the imaging conditions, the irradiation field obtaining unit 115 obtains the preset irradiation field information as irradiation field information in radiation imaging.

Note that this processing is exemplary, and image processing based on the first irradiation field obtaining method may be replaced with processing based on information (irradiation field information concerning radiation imaging which is preset as imaging conditions) included in imaging conditions for the second irradiation field obtaining method. For example, the irradiation field obtaining unit 115 performs the obtaining processing of obtaining irradiation field information in radiation imaging, as the first irradiation field obtaining method, based on irradiation field information in radiation imaging which is preset as imaging conditions (step S103). If no irradiation field information is preset and no irradiation field information can be obtained by the obtaining processing in step S103, the irradiation field obtaining unit 115 obtains irradiation field information based on image processing, as the second irradiation field obtaining method, for a radiation image (step S105).

A procedure in the flowchart of FIG. 2 will be described below. In step S101, the image obtaining unit 114 obtains a radiation image from the radiation imaging apparatus 103.

In step S102, the imaging information obtaining unit 113 obtains, for example, a tube voltage, tube current, irradiation time, and mAs value as imaging information in radiation imaging from the radiation generating apparatus 102. The imaging information obtaining unit 113 obtains an SOD from information preset in the imaging control apparatus 101.

This embodiment has exemplified the case in which an SOD is obtained from information preset in the imaging control apparatus 101. However, this is not exhaustive. For example, the imaging information obtaining unit 113 may obtain an SID as imaging information from the radiation generating apparatus 102.

In step S103, the irradiation field obtaining unit 115 obtains an irradiation field in radiation imaging by applying the first irradiation field obtaining method to the obtained radiation image. Although one of various methods can be used as the first irradiation field obtaining method, an example of using image processing as the first irradiation field obtaining method will be described below. The irradiation field obtaining unit 115 acquires a radiation image, scans the radiation image, and executes image processing for recognizing a region (irradiation field) irradiated with radiation.

Radiation that is transmitted through a subject is weak relative to radiation that is not transmitted through the subject. Based on this characteristic, the irradiation field obtaining unit 115 can distinguishly recognize a region transmitted through a subject (to be referred as a "subject region" hereinafter) and a region where the radiation imaging apparatus 103 (sensor) is directly irradiated with radiation (to be referred as a "direct irradiated region" hereinafter) in the radiation image.

The irradiation field obtaining unit 115 recognizes, for example, a direct irradiated region of an obtained radiation image from pixel values based on image processing, and can obtain a subject region by excluding the direct irradiated region from the radiation image. The irradiation field obtaining unit 115 can also obtain a subject region or irradiation field information based on the pixel values of the radiation image obtained by image processing.

An analysis algorithm for image processing in the first irradiation field obtaining method is an algorithm corresponding to each imaging portion. When executing image processing based on this analysis algorithm, the irradiation field obtaining unit 115 can recognize an imaging portion (region of interest) of a subject from a radiation image and use information concerning the recognized imaging portion of the subject for the first irradiation field obtaining method. The irradiation field obtaining unit 115 can also obtain irradiation field information by executing image processing using portion information preset by the imaging condition setting unit 112. The irradiation field obtaining unit 115 can also obtain irradiation field information based on shape information obtained by recognizing the edge portion of a subject from a radiation image based on image processing.

In step S104, the irradiation field obtaining unit 115 determines whether irradiation field information was able to be obtained by the image processing in step S103. Assume that image processing is used as the first irradiation field obtaining method. In this case, if one of the following conditions as determination conditions is met, the irradiation field obtaining unit 115 determines that irradiation field information cannot be obtained by the first irradiation field obtaining method.

When image processing is to be used, there are quite a few cases in which an irradiation field cannot be accurately obtained, regardless of the image processing technique in use. For example, various types of determination conditions can be conceived, including a case in which a predetermined area of a direct irradiated region was not able to be recognized from pixel values, a case in which a predetermined area of an irradiation field or subject region was not able to be recognized from pixel values, a case in which an imaging portion of a subject was not able to be specified in a radiation image, a case in which preset portion information differs from portion information specified from a radiation image, a case in which an edge of a subject was not able to be specified in a radiation image, a cased in which a predetermined area of a subject specified by an edge was not able to be recognized, or a case in which it is determined that an irradiation field differs from an irradiation field of a subject assumed by an operator.

Upon determining in step S104 that no irradiation field information was able to be obtained (YES in step S104), the irradiation field obtaining unit 115 advances the process to step S106. In contrast to this, upon determining in step S104 that no irradiation field information was able to be obtained (NO in step S104), the irradiation field obtaining unit 115 advances the process to step S105.

In step S105, the irradiation field obtaining unit 115 obtains irradiation field information based on the second irradiation field obtaining method. In this case, as the second irradiation field obtaining method, the irradiation field obtaining unit 115 uses irradiation field information in which an irradiation field used for radiation imaging is preset before imaging. The irradiation field obtaining unit 115 then advances the process to step S106.

In step S106, the area dose obtaining unit 116 obtains the area of an irradiation field based on the irradiation field information obtained in step S103 or S105. The area dose obtaining unit 116 then obtains an area dose based on the imaging information obtained by the imaging information obtaining unit 113 by using a simplified dose obtaining method such as an NDD method. The area dose obtaining unit 116 obtains an area dose based on the area of an irradiation field and the irradiation dose obtained by using the simplified dose obtaining method. For example, the area dose obtaining unit 116 can obtain an area dose by multiplying an obtained irradiation dose by the area of the irradiation field.

In step S107, the display control unit 117 performs display control to cause the display unit to display the area dose obtained in step S106.

(Image Processing or Processing Using Collimator Information in Radiation Generating Apparatus)

Figure 3:
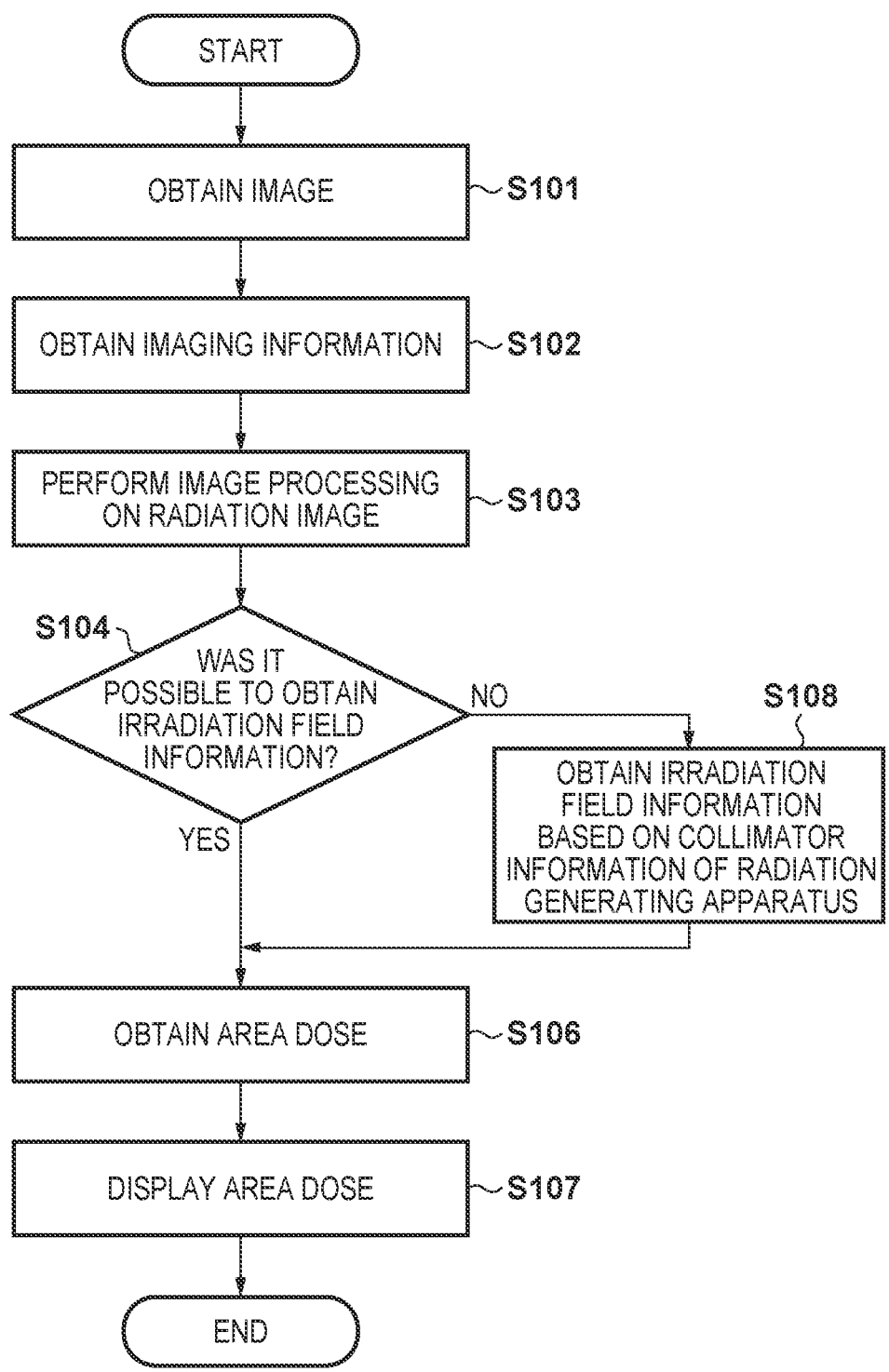
FIG. 3 is a flowchart for explaining a procedure for processing according to the first embodiment.

FIG. 3 explains a procedure for processing according to the first embodiment, and is a flowchart for explaining a procedure for the processing of obtaining an area dose and displaying the obtained area dose.

In the flowchart of FIG. 3, the irradiation field obtaining unit 115 performs image processing for a radiation image as the first irradiation field obtaining method (step S103). In a case no irradiation field information can be obtained in image processing, the irradiation field obtaining unit 115 obtains irradiation field information based on information included in imaging information as the second irradiation field obtaining method (step S105). That is, the irradiation field obtaining unit 115 obtains irradiation field information based on collimator information concerning the radiation generating apparatus which is included in imaging information (step S105).

In the flowchart described with reference to FIG. 2, in the second irradiation field obtaining method (step S105), a method using irradiation field information preset as irradiation field information used for actual imaging before imaging is used as an example. Referring to FIG. 3, the irradiation field obtaining unit 115 obtains collimator information from the radiation generating apparatus 102 (step S108) instead of preset irradiation field information (step S105 in FIG. 2).

Note that this processing is exemplary, and the image processing in the first irradiation field obtaining method may be replaced with processing based on information included in imaging information in the second irradiation field obtaining method. For example, the irradiation field obtaining unit 115 performs the obtaining processing of obtaining irradiation field information based on information included in imaging information as the first irradiation field obtaining method (step S103). If no irradiation field information can be obtained by the obtaining processing in step S103, the irradiation field obtaining unit 115 can obtain irradiation field information based on image processing for a radiation image as the second irradiation field obtaining method (step S105).

A procedure in the flowchart of FIG. 3 will be described below. The same step numbers as those in FIG. 2 denote the steps with the same processing contents as in the flowchart of FIG. 3, and a description of overlapping processing contents will be simplified.

The procedure for the processing in steps S101 to step S103 is the same as that in FIG. 2. Upon determining in step S104 that irradiation field information was able to be obtained (YES in step S104), the irradiation field obtaining unit 115 advances the process to step S106. In contrast to this, upon determining in step S104 that no irradiation field information was able to be obtained (NO in step S104), the irradiation field obtaining unit 115 advances the process to step S108.

In step S108, the irradiation field obtaining unit 115 obtains irradiation field information based on the second irradiation field obtaining method. In this case, the irradiation field obtaining unit 115 obtains collimator information after imaging from the radiation generating apparatus 102 as the second irradiation field obtaining method. The irradiation field obtaining unit 115 can obtain irradiation field information based on the collimator information obtained from the radiation generating apparatus 102. The irradiation field obtaining unit 115 can estimate irradiation field information by using the collimator information and an SID that is the distance between the radiation generating apparatus 102 and the detection surface of the radiation imaging apparatus 103. The irradiation field obtaining unit 115 then advances the process to step S106.

Note that as the second irradiation field obtaining method, for example, the operator operates the input unit to allow the irradiation field obtaining unit 115 to set irradiation field information based on adjusted (manually input) information. For example, the operator can operate the input unit to set the entire surface (effective pixel region) of the radiation imaging apparatus 103 as an irradiation field. The irradiation field obtaining unit 115 can also obtain irradiation field information based on a default value.

In step S106, the area dose obtaining unit 116 obtains the area of an irradiation field based on the irradiation field information obtained in step S103 or S108. The area dose obtaining unit 116 obtains an area dose based on the area of the irradiation field and the irradiation dose obtained by using the simplified dose obtaining method.

In step S107, the display control unit 117 performs display control to cause the display unit to display the area dose obtained in step S106.

(Notification Display in a Case No Irradiation Field Information can be Obtained)

An arrangement configured to perform notification display to indicate that no area dose can be obtained in a case no irradiation field information can be obtained will be described next. In a case no irradiation field information can be obtained, the display control unit 117 performs display control to cause the display unit 104 to perform notification display to indicate that no area dose can be obtained.

Figure 4:
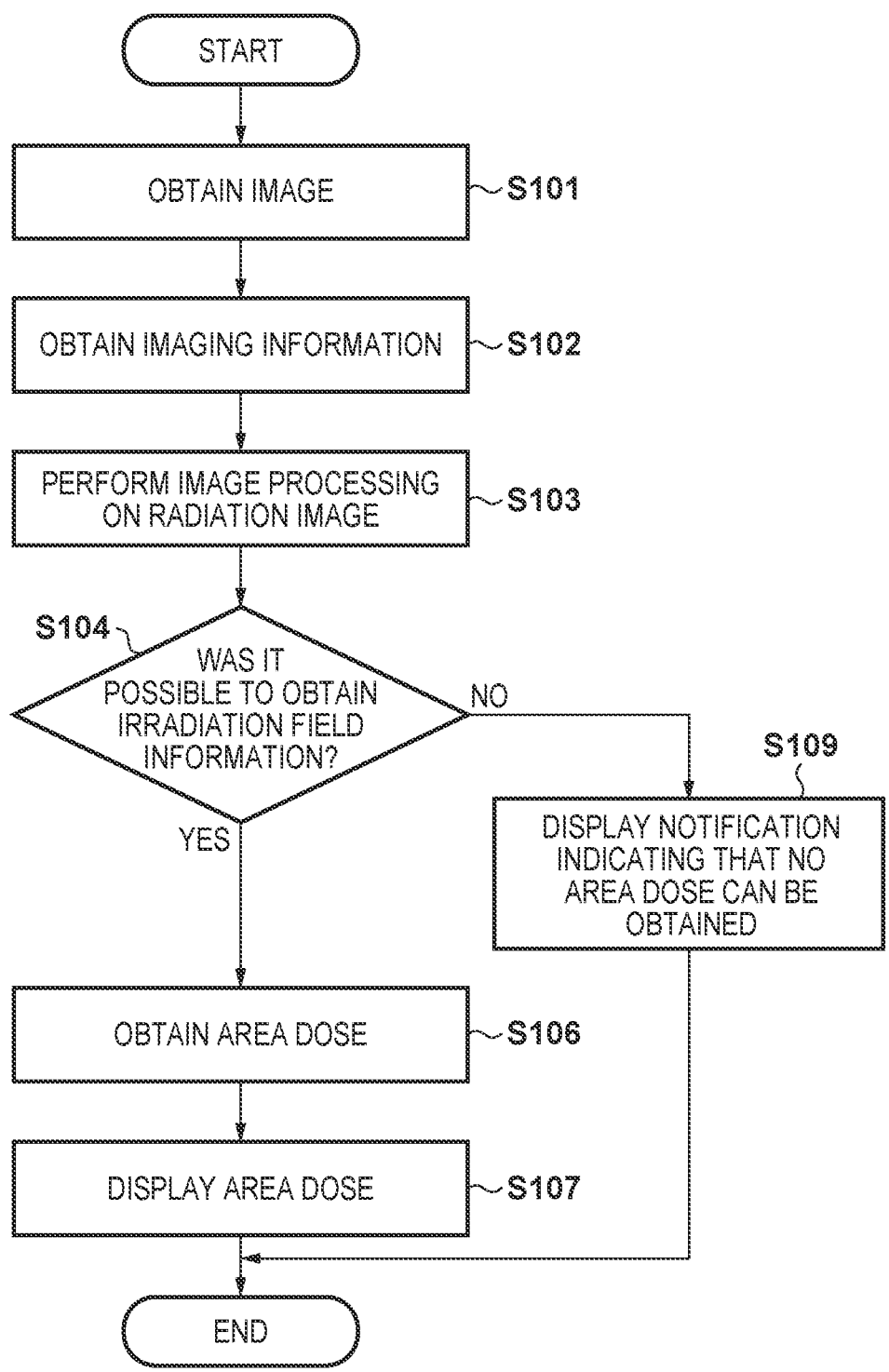
FIG. 4 is a flowchart for explaining a procedure for processing according to the first embodiment.

FIG. 4 explains a procedure for processing according to the first embodiment, and is a flowchart for explaining a procedure for the processing of obtaining an area dose and displaying the obtained area dose. The flowchart described with reference to FIG. 2 has exemplified the case of using irradiation field information in which an irradiation field to be used for actual imaging before imaging is preset in the second irradiation field obtaining method (step S105). The flowchart described with reference to FIG. 3 has exemplified the case of obtaining collimator information from the radiation generating apparatus 102 in the second irradiation field obtaining method (step S108).

Referring to FIG. 4, if no irradiation field information can be obtained (NO in step S104) by the first irradiation field obtaining method (step S103), display control is performed (step S109) to cause the display unit to perform notification display to indicate that no area dose can be obtained instead of executing the second irradiation field obtaining method (steps S105 and S108). The same step numbers as those in FIG. 2 denote the steps with the same processing contents as in the flowchart of FIG. 4, and a description of overlapping processing contents will be simplified.

Processing in steps S101 to S103 is the same as the procedures for the processing in FIGS. 2 and 3. Upon determining in step S104 that irradiation field information was able to be obtained (YES in step S104), the irradiation field obtaining unit 115 advances the process to step S106.

In step S106, the area dose obtaining unit 116 obtains the area of an irradiation field based on the irradiation field information obtained in step S103. The area dose obtaining unit 116 then obtains an area dose based on the area of the irradiation field and the irradiation dose obtained by using the simplified dose obtaining method.

In step S107, the display control unit 117 performs display control to cause the display unit to display the area dose obtained in step S106.

Upon determining in step S104 that no irradiation field information can be obtained (NO in step S104), the irradiation field obtaining unit 115 advances the process to step S109.

In step S109, the display control unit 117 performs display control to cause the display unit to display a notification indicating that no area dose can be obtained. As notification display, for example, the display control unit 117 can cause the display unit to display an error message or display information such as "#N/A" indicating that no area dose was able to be calculated.

The display control in step S107 makes it possible to obtain an irradiation field used for actual imaging and display an accurate area dose.

In contrast, the display control in step S109 makes it possible to present the operator with information indicating that no area dose can be obtained based on the irradiation field information used for actual imaging instead of executing the second irradiation field obtaining method, in a case no irradiation field information was able to be obtained in step S103 (the first irradiation field obtaining method).

(Processing Based on Different Image Processing)

Figure 5:
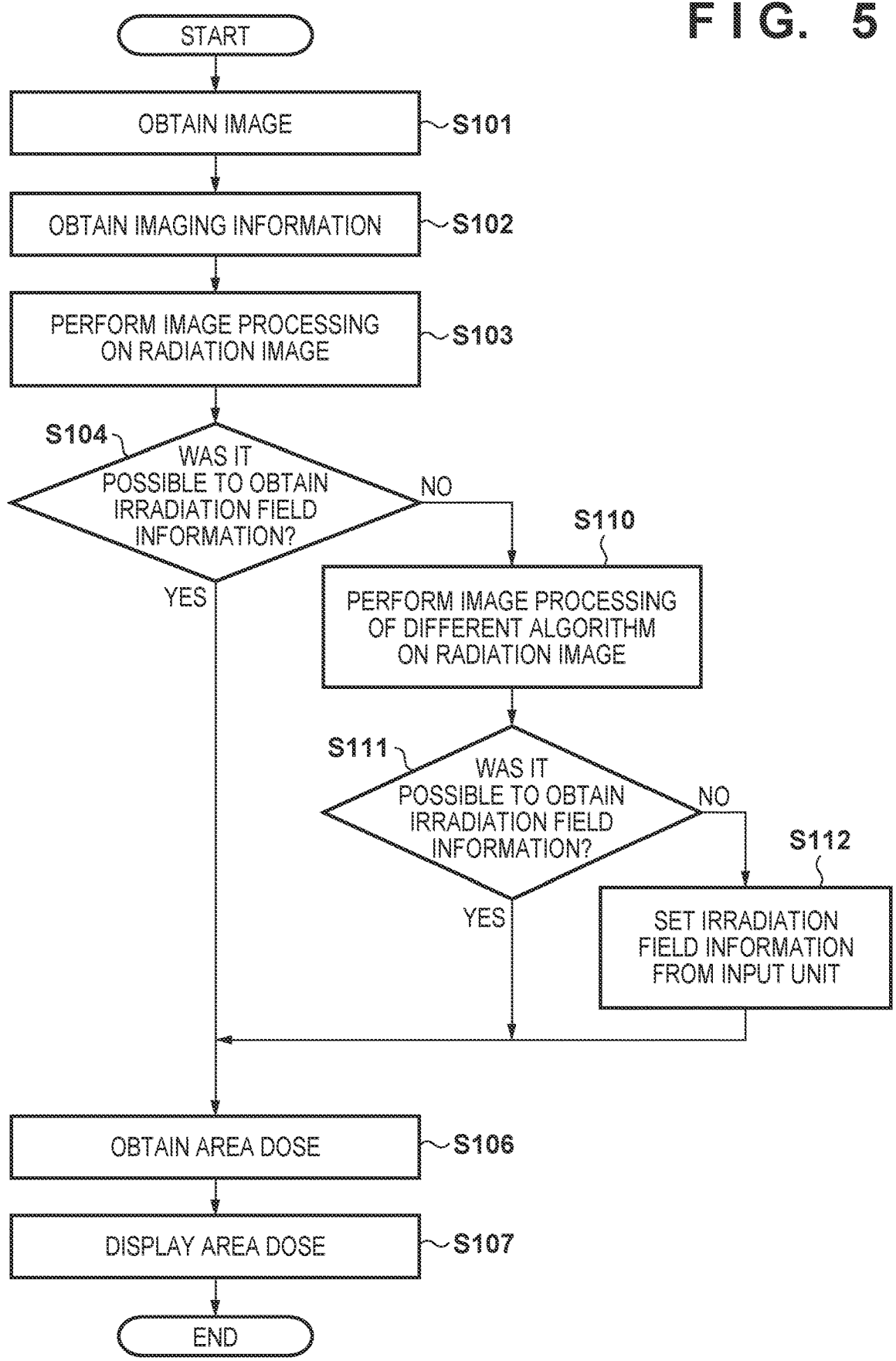
FIG. 5 is a flowchart for explaining a procedure for processing according to the first embodiment.

FIG. 5 explains a procedure for processing according to the first embodiment, and is a flowchart for explaining a procedure for the processing of obtaining an area dose and displaying the obtained area dose.

In the flowchart of FIG. 5, the irradiation field obtaining unit 115 performs image processing for a radiation image as the first irradiation field obtaining method (step S103). In image processing, in a case no irradiation field information can be obtained, irradiation field obtaining unit 115 performs image processing of a different image processing algorithm to the first irradiation field obtaining method as the second irradiation field obtaining method (step S110), thereby obtaining irradiation field information.

The flowchart described with reference to FIG. 2 has exemplified the method using irradiation field information preset as irradiation field information used for actual imaging before imaging in the second irradiation field obtaining method (step S105). Referring to FIG. 5, the irradiation field obtaining unit 115 obtains an irradiation field in radiation imaging based on an image processing algorithm different from the image processing algorithm used in the first irradiation field obtaining method (steps S110 and S111) instead of using preset irradiation field information (step S105 in FIG. 2).

Image processing in the first irradiation field obtaining method (step S103) is processing based on an algorithm corresponding to each imaging portion, and image processing in the second irradiation field obtaining method (step S110) is processing based on an algorithm that is not limited by an imaging portion. It is possible to set an algorithm corresponding to each imaging portion based on imaging conditions. In addition, for example, the operator can select an algorithm corresponding to each imaging portion via the input unit.

A procedure in the flowchart of FIG. 5 will be described below. The same step numbers as those in FIG. 2 denote the steps with the same processing contents as in the flowchart of FIG. 5, and a description of overlapping processing contents will be simplified.

Processing in steps S101 to S103 is the same as the procedures for the processing in FIG. 2. Upon determining in step S104 that irradiation field information was able to be obtained (YES in step S104), the irradiation field obtaining unit 115 advances the process to step S106. In contrast to this, upon determining in step S104 that no irradiation field information can be obtained (NO in step S104), the irradiation field obtaining unit 115 advances the process to step S110.

In step S110, the irradiation field obtaining unit 115 obtains an irradiation field in radiation imaging by applying the second irradiation field obtaining method (image processing based on another algorithm) for the obtained radiation image.

The irradiation field obtaining unit 115 acquires a radiation image, scans the radiation image, and executes image processing for recognizing a region (irradiation field) irradiated with radiation. An image processing algorithm in the second irradiation field obtaining method executed by the irradiation field obtaining unit 115 differs from an image processing algorithm in the first irradiation field obtaining method.

The image processing (the first image processing) in the first irradiation field obtaining method is processing based on an algorithm corresponding to each imaging portion. Using an algorithm corresponding to each imaging portion makes it possible to obtain irradiation field information more accurately. In contrast to this, the image processing (the second image processing) in the second irradiation field obtaining method is processing based on an algorithm that is not limited by a specific imaging portion. Even if no irradiation field information can be obtained by image processing in the first irradiation field obtaining method because of differences between imaging portions or depending on imaging conditions, the recognition rate of irradiation fields can be improved by applying image processing in the second irradiation field obtaining method.

In step S111, the irradiation field obtaining unit 115 determines whether irradiation field information was able to be obtained by image processing based on another algorithm in step S110. Determination conditions in step S111 are the same as those in step S104.

Upon determining in step S111 that irradiation field information was able to be obtained (YES in step S111), the irradiation field obtaining unit 115 advances the process to step S106. Upon determining in step S111 that no irradiation field information can be obtained (NO in step S111), the irradiation field obtaining unit 115 advances the process to step S112.

In step S112, the irradiation field obtaining unit 115 sets an irradiation field by using a third irradiation field obtaining method. As the third irradiation field obtaining method, the irradiation field obtaining unit 115 can set irradiation field information based on information adjusted (manually input) by the operator with the input unit. For example, operating the input unit makes it possible to set the entire surface (effective pixel region) of the radiation imaging apparatus 103 as an irradiation field.

Note that the irradiation field obtaining unit 115 can obtain irradiation field information based on step S105 (preset irradiation field information) in FIG. 2 and step S108 in FIG. 3 (the collimator information obtained from the radiation generating apparatus 102), as the third irradiation field obtaining method in step S112. Alternatively, if no irradiation field information can be obtained by the second irradiation field obtaining method (step S111) (NO in step S111), the display control unit 117 can also perform display control to cause the display unit to perform display notification indicating that no area dose can be obtained instead of executing the third irradiation field obtaining method, as described with reference to the processing in step S109 in FIG. 4.

Figure 6:
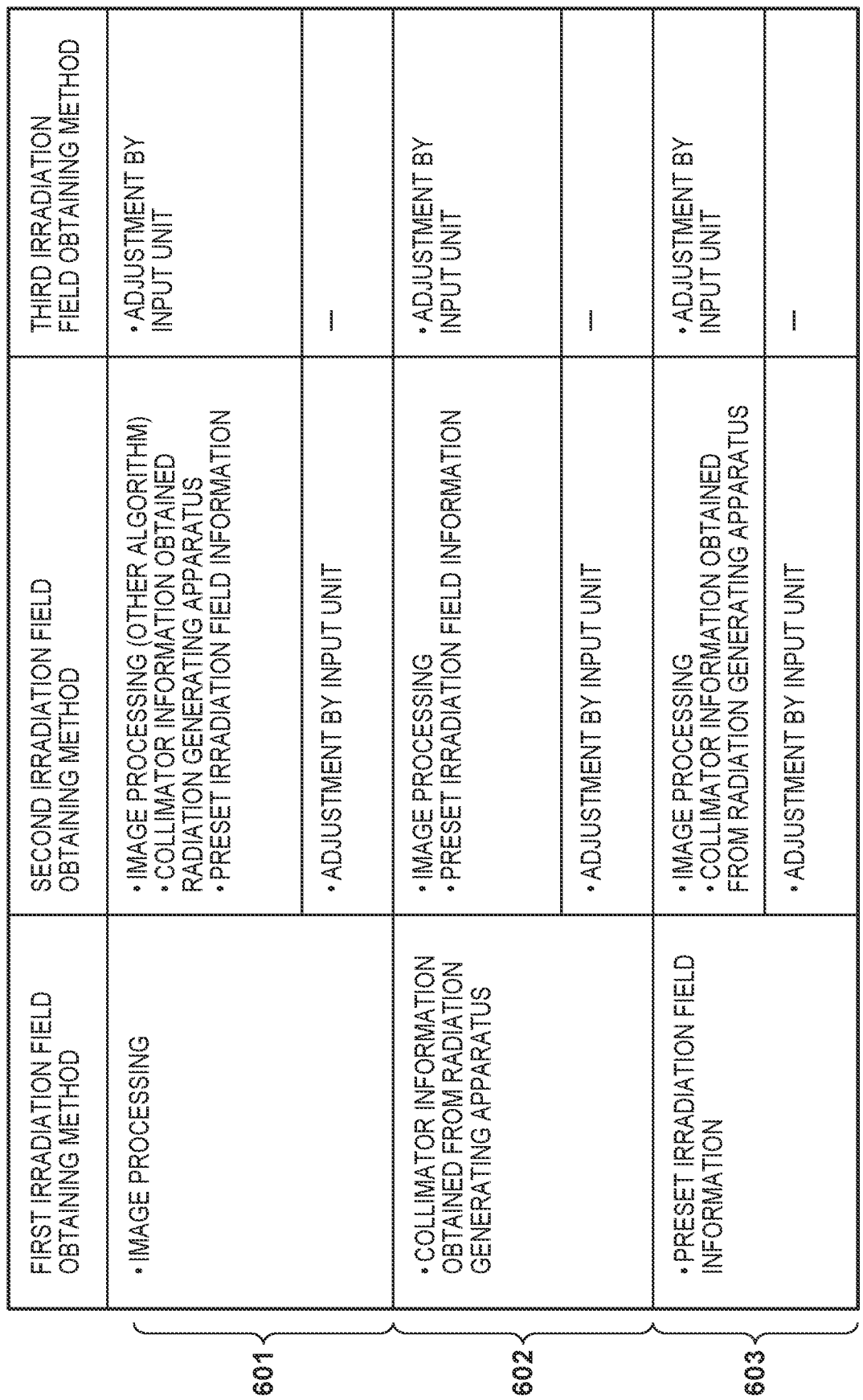
FIG. 6 is a view exemplarily showing the contents of processing by a first irradiation field obtaining method, a second irradiation field obtaining method, and a third irradiation field obtaining method.

FIG. 6 exemplarily shows the contents of processing in the first irradiation field obtaining method, the second irradiation field obtaining method, and the third irradiation field obtaining method. Settings 601 in FIG. 6 correspond to processing in each flowchart described with reference to FIGS. 2 to 5.

That is, according to the settings 601, the irradiation field obtaining unit 115 obtains irradiation field information based on analysis on the radiation image based on image processing as the first irradiation field obtaining method. In this case, if no irradiation field information can be obtained by the image processing in the first irradiation field obtaining method, the irradiation field obtaining unit 115 can set irradiation field information based on analysis on a radiation image by image processing based on another algorithm, the collimator information obtained by the radiation generating apparatus 102, preset irradiation field information, or the information adjusted (manually input) by the operator with the input unit, as the second irradiation field obtaining method.

In the second irradiation field obtaining method, if no irradiation field information can be obtained by analysis on a radiation image based on image processing based on another algorithm, the irradiation field obtaining unit 115 can set irradiation field information based on the information adjusted (manually input) by the operator with the input unit, as the third irradiation field obtaining method.

The processing in each of the flowcharts described with reference to FIGS. 2 to 5 has exemplified the case of using image processing as the first irradiation field obtaining method. However, the first irradiation field obtaining method may be a method of obtaining irradiation field information based on collimator information concerning the radiation generating apparatus 102. Alternatively, as the first irradiation field obtaining method, irradiation field information may be obtained based on preset irradiation field information.

In a case the imaging information obtaining unit 113 can obtain no imaging information by the first irradiation field obtaining method, the irradiation field obtaining unit 115 can obtain irradiation field information based on image processing corresponding to a radiation image or preset irradiation field information as the second irradiation field obtaining method.

For example, referring to FIG. 6, settings 602 exemplarily show a case in which irradiation field information is obtained based on the collimator information obtained from the radiation generating apparatus 102 as the first irradiation field obtaining method. In this case, in a case no collimator information can be obtained from the radiation generating apparatus 102, the irradiation field obtaining unit 115 can set irradiation field information based on analysis on a radiation image by image processing, preset irradiation field information, or the information adjusted (manually input) by the operator with the input unit, as the second irradiation field obtaining method.

In a case no irradiation field information can be obtained by analysis on a radiation image based on image processing, the irradiation field obtaining unit 115 can set irradiation field information based on information adjusted (manually input) by the operator with the input unit as the third irradiation field obtaining method.

In a case no irradiation field information is preset as the first irradiation field obtaining method, the irradiation field obtaining unit 115 can obtain irradiation field information based on image processing for a radiation image or information included in imaging information concerning radiation imaging as the second irradiation field obtaining method.

For example, settings 603 in FIG. 6 exemplarily show a case in which the irradiation field obtaining unit 115 obtains irradiation field information based on preset irradiation information as the first irradiation field obtaining method. In this case, in a case no irradiation field information is preset, the irradiation field obtaining unit 115 can set irradiation field information based on analysis on a radiation image by image processing, the collimator information obtained by the radiation generating apparatus 102, or the information adjusted (manually input) by the operator with the input unit, as the second irradiation field obtaining method.

The imaging control apparatus 101 includes the input unit for inputting irradiation field information. As shown in FIG. 6, in a case no irradiation field information can be obtained by the first irradiation field obtaining method or the second irradiation field obtaining method, the irradiation field obtaining unit 115 obtains input irradiation field information as irradiation field information in radiation imaging, as the third irradiation field obtaining method. That is, in a case no irradiation field information can be obtained by analysis on the radiation image based on image processing, the irradiation field obtaining unit 115 can set irradiation field information based on information adjusted (manually input) by the operator with the input unit as the third irradiation field obtaining method.

According to this embodiment, it is possible to obtain an area dose based on irradiation field information in executed radiation imaging.

Second Embodiment

The second embodiment will exemplify an arrangement in which an input unit 201 is connected to the imaging control apparatus 101 described in the first embodiment, and the imaging control apparatus 101 performs imaging control based on an input instruction from the input unit 201.

In the second embodiment, in a case an instruction is input from the input unit 201 to change an imaging condition after radiation imaging, for example, an instruction to change irradiation field information in radiation imaging which is preset as information included in imaging conditions, an area dose obtaining unit 116 obtains an area dose based on the imaging conditions after the change, the irradiation dose obtained from the dose information table, and the area of the irradiation field. An irradiation field obtaining unit 115 also obtains irradiation field information by executing image processing using the imaging conditions after the change.

Figure 7:
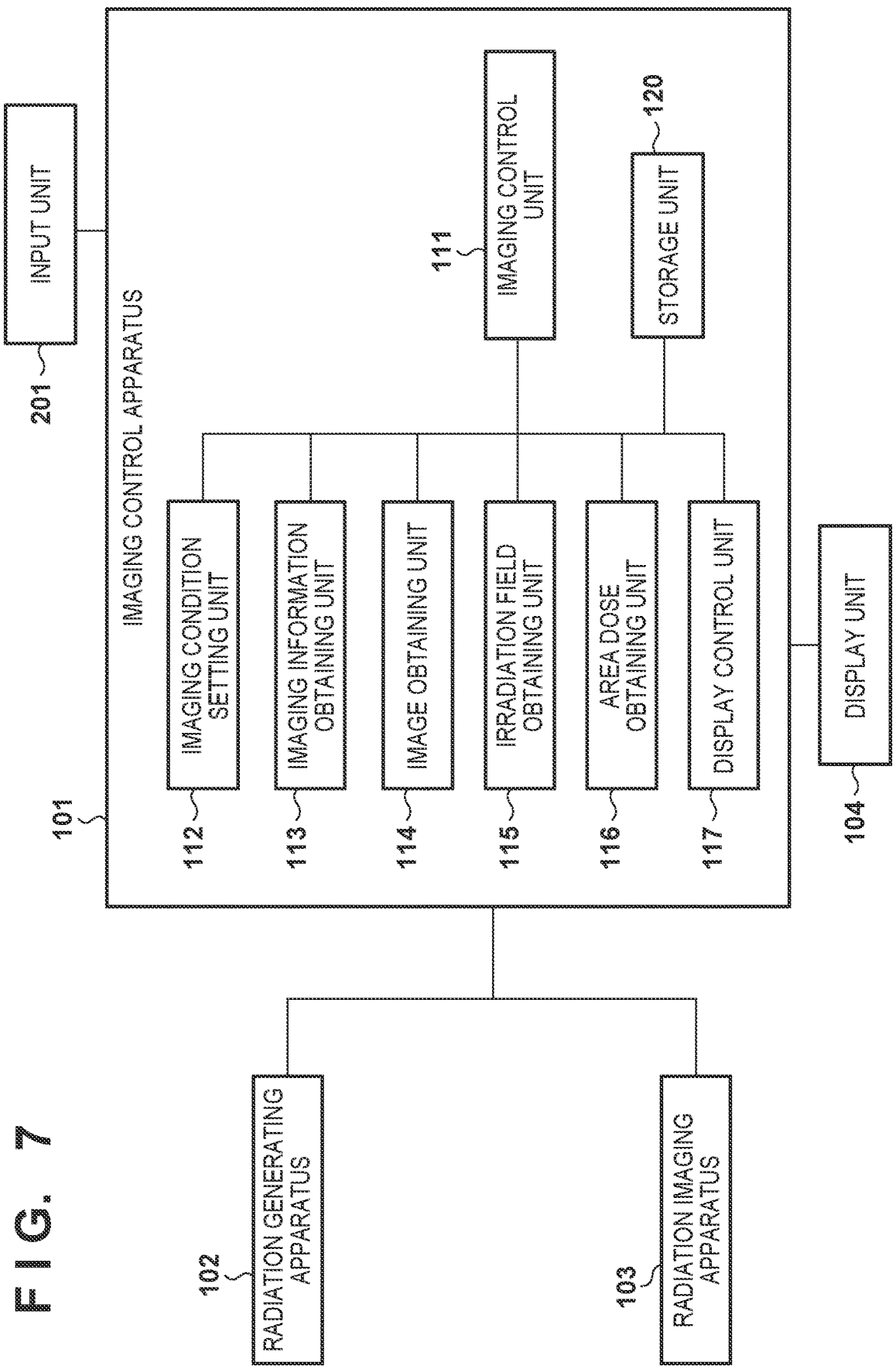
FIG. 7 is a block diagram exemplarily showing the arrangement of a radiation imaging system according to the second embodiment.

FIG. 7 is a block diagram exemplarily showing the arrangement of a radiation imaging system according to the second embodiment. An imaging control apparatus 101 controls radiation imaging by communicating with a radiation generating apparatus 102 and a radiation imaging apparatus 103 (radiation detector).

The arrangement of the imaging control apparatus 101 according to the second embodiment is the same as that according to the first embodiment. An imaging control unit 111 can control operations of the respective units of the imaging control apparatus 101 as functional components, including an imaging condition setting unit 112, an imaging information obtaining unit 113, an image obtaining unit 114, an irradiation field obtaining unit 115, the area dose obtaining unit 116, and a display control unit 117. An input unit 201 is connected to the imaging control apparatus 101, and the imaging control unit 111 of the imaging control apparatus 101 performs imaging control based on an input instruction from the input unit 201. Differences from the first embodiment will be mainly described below.

Figure 8:
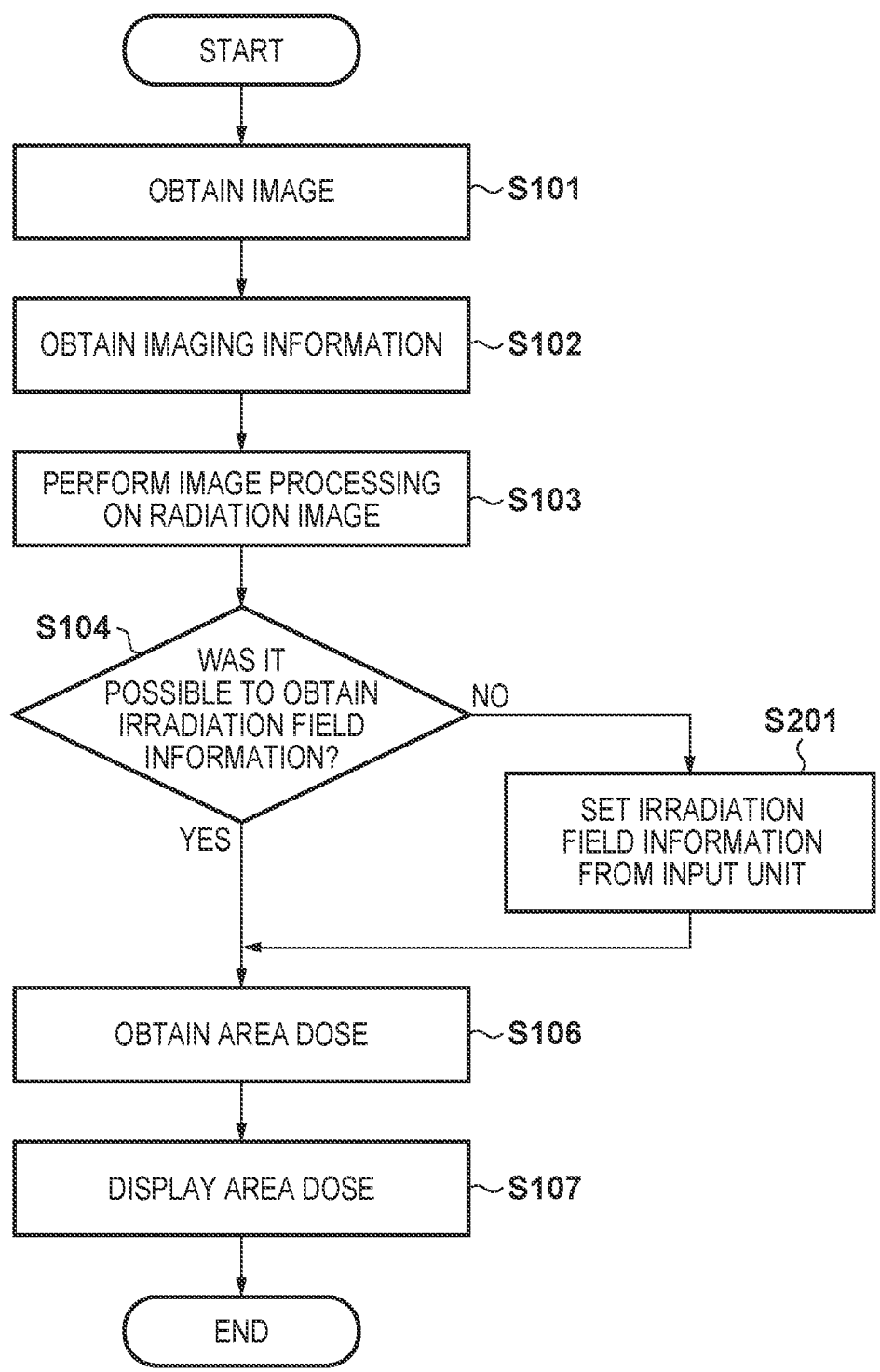
FIG. 8 is a flowchart for explaining a procedure for processing according to the second embodiment.

FIG. 8 explains a procedure in processing according to the second embodiment, and is a flowchart for explaining a procedure for the processing of obtaining an area dose and displaying the obtained area dose. The first embodiment has exemplified the case in which in a case no irradiation field information can be obtained (NO in step S104) by the first irradiation field obtaining method (step S103) in the flowchart of FIG. 2, preset irradiation field information is used as an irradiation field used for actual imaging before imaging in the second irradiation field obtaining method (step S105).

Referring to FIG. 8, if no irradiation field information can be obtained by the first irradiation field obtaining method (step S103) (No in step S104), irradiation field information is set by the input unit 201 (step S201). The same step numbers as those in FIG. 2 denote the steps with the same processing contents as in the flowchart of FIG. 8, and a description of overlapping processing contents will be simplified.

Processing in steps S101 to S103 is the same as the procedures for the processing in FIG. 2. Upon determining in step S104 that irradiation field information was able to be obtained (YES in step S104), the irradiation field obtaining unit 115 advances the process to step S106.

Upon determining in step S104 that no irradiation field information can be obtained (NO in step S104), the irradiation field obtaining unit 115 advances the process to step S201.

In step S201, the irradiation field obtaining unit 115 sets irradiation field information input from the input unit 201. The input unit 201 includes input devices such as a mouse and a keyboard. The operator can input irradiation field information from the input unit 201. In this step, the irradiation field obtaining unit 115 can set irradiation field information based on the information input by the operator with the input unit 201.

In step S106, the area dose obtaining unit 116 obtains the area of an irradiation field based on the irradiation field information obtained in step S103 or S201. The area dose obtaining unit 116 then obtains an area dose based on the area of the irradiation field and the irradiation dose obtained by using the simplified dose obtaining method.

In step S107, the display control unit 117 performs display control to cause the display unit to display the area dose obtained in step S106.

Figure 9:
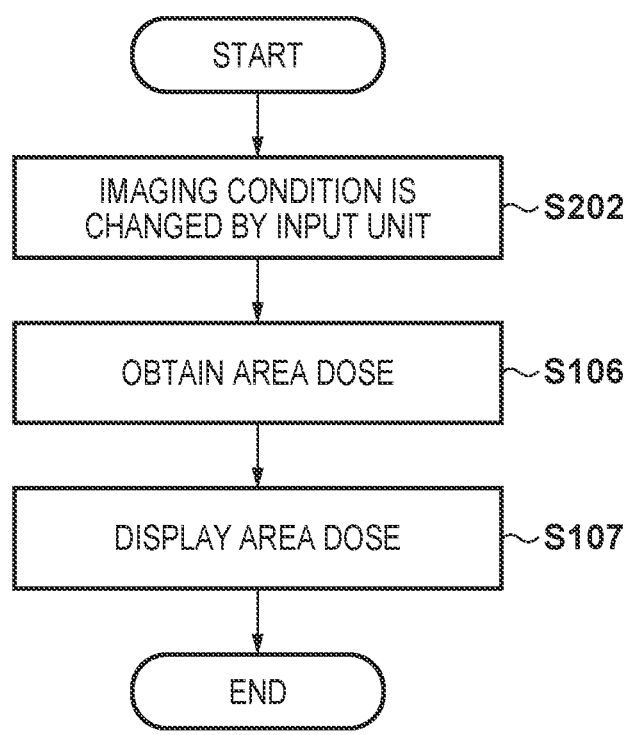
FIG. 9 is a flowchart for explaining a procedure for processing according to the second embodiment.

FIG. 9 is a flowchart for explaining a procedure in processing according to the second embodiment. FIG. 9 is not a flowchart at the time of imaging, but a flowchart for explaining a procedure for the processing of obtaining, in a case an imaging condition is changed by the input unit 201 after radiation imaging (step S202), an area dose based on imaging conditions after the change and displaying the obtained area dose.

In step S202, the operator operates the input unit 201 to change an imaging condition. The area dose obtaining unit 116 obtains the imaging condition after the change which is input from the input unit 201.

Reasons for changing imaging conditions (for example, portion information and an SOD) include, for example, a case in which portion information indicating a preset imaging portion is wrong and a case in which imaging is hastily executed under different imaging conditions. Assume that a simplified dose obtaining method such as an NDD method is used. In this case, in a case an imaging condition is changed, an area dose needs to be obtained again. For this reason, an area dose is obtained again in step S106, and is displayed in step S107.

In step S106, the area dose obtaining unit 116 obtains the area of an irradiation field based on the irradiation field information obtained in step S103 or S201. The area dose obtaining unit 116 then obtains information concerning an irradiation dose corresponding to the changed imaging condition by referring to the dose information table stored in a storage unit 120 based on the imaging conditions after the change which are input from the input unit 201. The area dose obtaining unit 116 then obtains an area dose based on the area of the irradiation field and the obtained irradiation dose.

In step S107, the display control unit 117 performs display control to cause the display unit to display the area dose obtained in step S106.

According to this embodiment, even in a case an imaging condition is changed after radiation imaging, an area dose can be obtained and displayed based on the imaging conditions after the change.

Assume that at the time of radiation imaging, in step S103 in FIG. 8, the irradiation field obtaining unit 115 has obtained irradiation field information by executing image processing using preset portion information. In this case, the irradiation field obtaining unit 115 can execute image processing by using portion information in which irradiation field information is set and obtain irradiation field information, based on the imaging condition (for example, portion information) changed after the radiation imaging.

Figure 10:
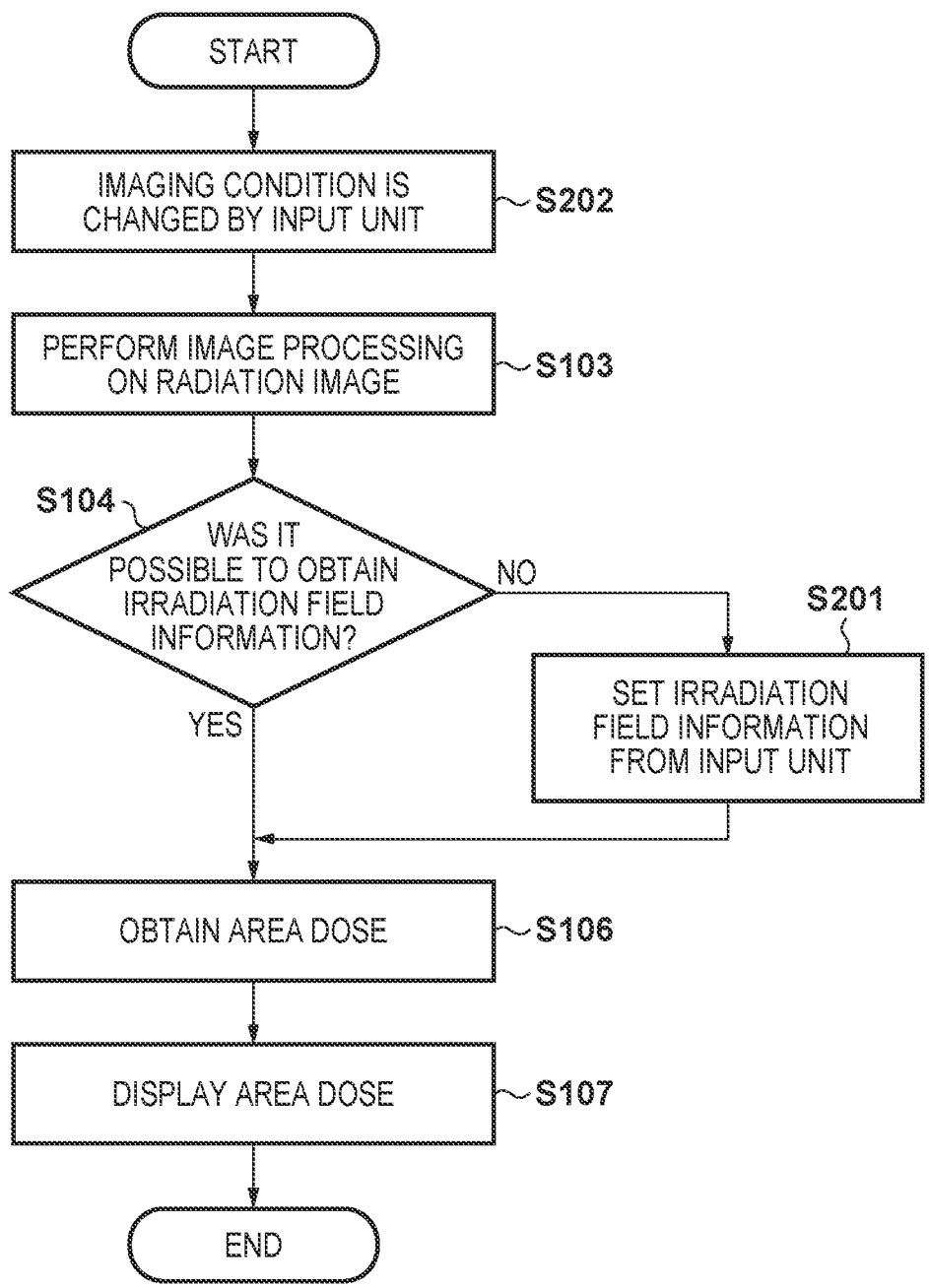
FIG. 10 is a flowchart for explaining a procedure for processing according to the second embodiment.

FIG. 10 explains a procedure for processing according to the second embodiment, and is a flowchart for explaining a procedure for the processing of obtaining an area dose based on changed imaging conditions and displaying the obtained area dose.

The flowchart of FIG. 10 explains a procedure for the processing of reexecuting, in a case an imaging condition is changed in step S202, the processing from step S103 in FIG. 8 based on the changed imaging condition, obtaining an area dose based on the changed imaging condition, and displaying the obtained area dose.

In step S202, the operator changes an imaging condition by operating the input unit 201. The irradiation field obtaining unit 115 and the area dose obtaining unit 116 obtain an imaging condition after the change which is input from the input unit 201.

In step S103, the irradiation field obtaining unit 115 obtains an irradiation field in radiation imaging by applying the first irradiation field obtaining method to the obtained radiation image. Although each of various types of methods can be used as the first irradiation field obtaining method, an example using image processing as the first irradiation field obtaining method will be described.

The irradiation field obtaining unit 115 acquires a radiation image, scans the radiation image, and executes image processing for the recognition of a region (irradiation field) irradiated with radiation. When executing image processing, the irradiation field obtaining unit 115 obtains irradiation field information by executing image processing using a changed imaging condition (for example, portion information).

Upon determining in step S104 that irradiation field information was able to be obtained by the processing in step S103 (YES in step S104), the irradiation field obtaining unit 115 advances the process to step S106.

Upon determining in step S104 that no irradiation field information can be obtained (NO in step S104), the irradiation field obtaining unit 115 advances the process to step S201.

In step S201, the irradiation field obtaining unit 115 sets irradiation field information input from the input unit 201 as the second irradiation field obtaining method. The irradiation field obtaining unit 115 can set irradiation field information based on the information input by the operator with the input unit 201.

In step S106, the area dose obtaining unit 116 obtains the area of an irradiation field based on the irradiation field information obtained in step S103 or S201. The area dose obtaining unit 116 then obtains an area dose based on the area of the irradiation field and the irradiation dose obtained by using the simplified dose obtaining method.

In step S107, the display control unit 117 performs display control to cause the display unit to display the area dose obtained in step S106.

This flowchart has exemplified a case in which upon determining in step S104 that no irradiation field information can be obtained, the irradiation field obtaining unit 115 sets irradiation field information based on the information input from the input unit 201 as the second irradiation field obtaining method (step S201). However, another setting method can be used as the second irradiation field obtaining method.

For example, as described with reference to FIG. 2, irradiation field information in which an irradiation field used for actual imaging before imaging is preset may be used as the second irradiation field obtaining method (step S105).

In addition, as shown in FIG. 3, as the second irradiation field obtaining method, irradiation field information may be obtained based on collimator information from the radiation generating apparatus 102 (step S108). Alternatively, as described with reference to FIG. 4, in a case no irradiation field information can be obtained by the first irradiation field obtaining method (step S103), it is possible to perform display control to cause the display unit to perform display notification indicating that no area dose can be obtained (step S109).

As described with reference to FIG. 5, it is also possible to obtain an irradiation field in radiation imaging by applying the second irradiation field obtaining method (image processing based on another algorithm) to an obtained radiation image (step S110). If no irradiation field information can be obtained even by applying the second irradiation field obtaining method (image processing based on another algorithm) (NO in step S111), the irradiation field obtaining unit 115 can also set irradiation field information based on the information based on processing in step S201 in FIG. 10, that is, the information input from the input unit 201 as the third irradiation field obtaining method (step S201).

According to this embodiment, even in a case an imaging condition is changed after radiation imaging, it is possible to obtain an area dose from the irradiation field information and the irradiation dose obtained based on the imaging conditions after the change and display the area dose.

Third Embodiment

The first and second embodiments each have exemplified the arrangement of the radiation imaging system including the single radiation imaging apparatus 103. The third embodiment will exemplify the arrangement of a radiation imaging system that includes a plurality of radiation imaging apparatuses and can perform, for example, long-length imaging by simultaneously irradiating a plurality of radiation imaging apparatuses with radiation from a radiation generating apparatus 102.

According to the third embodiment, an image obtaining unit 114 obtains a plurality of radiation images obtained by a plurality of radiation imaging apparatuses 103 and 301 by single irradiation with radiation from the radiation generating apparatus 102. The image obtaining unit 114 generates a long-length image by using the plurality of obtained radiation images.

Figure 11:
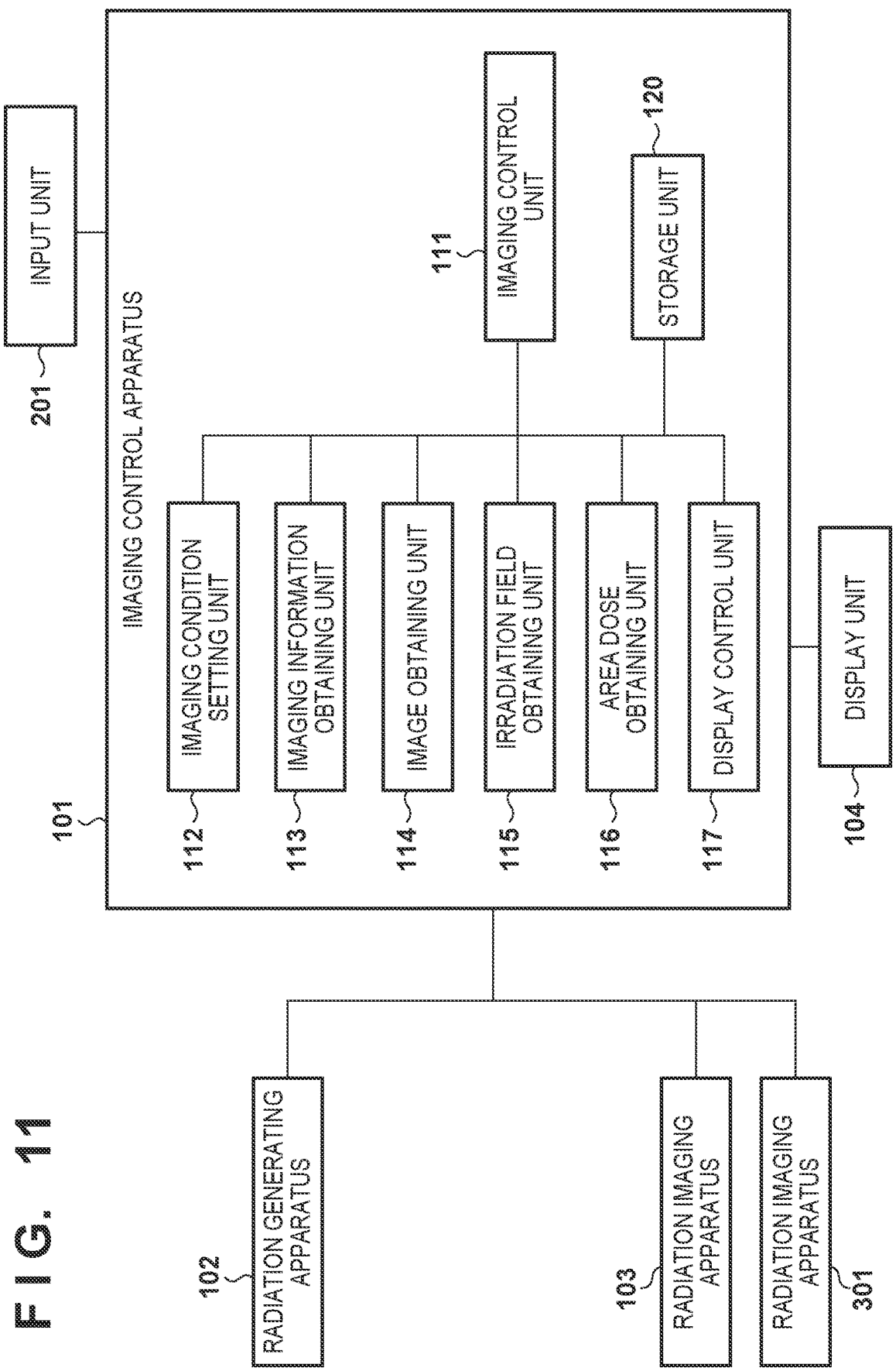
FIG. 11 is a block diagram exemplarily showing the arrangement of a radiation imaging system according to the third embodiment.

FIG. 11 exemplarily shows the arrangement of the radiation imaging system according to the third embodiment. An imaging control apparatus 101 controls radiation imaging by communicating with the radiation generating apparatus 102, the radiation imaging apparatus 103 (radiation detector), and the radiation imaging apparatus 301 (radiation detector). The radiation imaging apparatus 103 and the radiation imaging apparatus 301 make transition to an imaging ready state in accordance with an instruction from the imaging control apparatus 101, and perform radiation imaging in synchronism with the radiation generating apparatus 102.

The arrangement of the radiation imaging system shown in FIG. 11 is equivalent to the arrangement (FIG. 7) of the radiation imaging system according to the second embodiment to which the radiation imaging apparatus 301 is added. Note that the arrangement of the radiation imaging apparatuses 103 and 301 is exemplary, and using three or more radiation imaging apparatuses makes it also possible to perform long-length imaging.

Radiation applied from the radiation generating apparatus 102 to the plurality of radiation imaging apparatuses 103 and 301 (radiation detectors) is transmitted through a subject and reaches the plurality of radiation imaging apparatuses 103 and 301 (radiation detectors) to be simultaneously detected.

The image obtaining unit 114 obtains a plurality of radiation images obtained by the plurality of radiation imaging apparatuses 103 and 301 by single irradiation with radiation from the radiation generating apparatus 102. The image obtaining unit 114 can generate a long-length image by using the plurality of obtained radiation images.

The irradiation field obtaining unit 115 obtains irradiation field information in radiation imaging. The irradiation field obtaining unit 115 can obtain irradiation field information in radiation imaging based on the radiation image obtained by each of the plurality of radiation imaging apparatuses 103 and 301. In addition, the irradiation field obtaining unit 115 can obtain irradiation field information in radiation imaging based on the long-length image formed by using the plurality of radiation images obtained by the plurality of radiation imaging apparatuses 103 and 301.

The irradiation field obtaining unit 115 can also obtain irradiation field information by using the imaging conditions set by the imaging condition setting unit 112 or the imaging information obtained by the imaging information obtaining unit 113.

The area dose obtaining unit 116 obtains the area of an irradiation field based on irradiation field information obtained by the irradiation field obtaining unit 115. The area dose obtaining unit 116 then obtains an area dose by using a simplified dose obtaining method such as an NDD method based on the imaging information obtained by the imaging information obtaining unit 113 or the imaging conditions set by the imaging condition setting unit 112.

Figure 12:
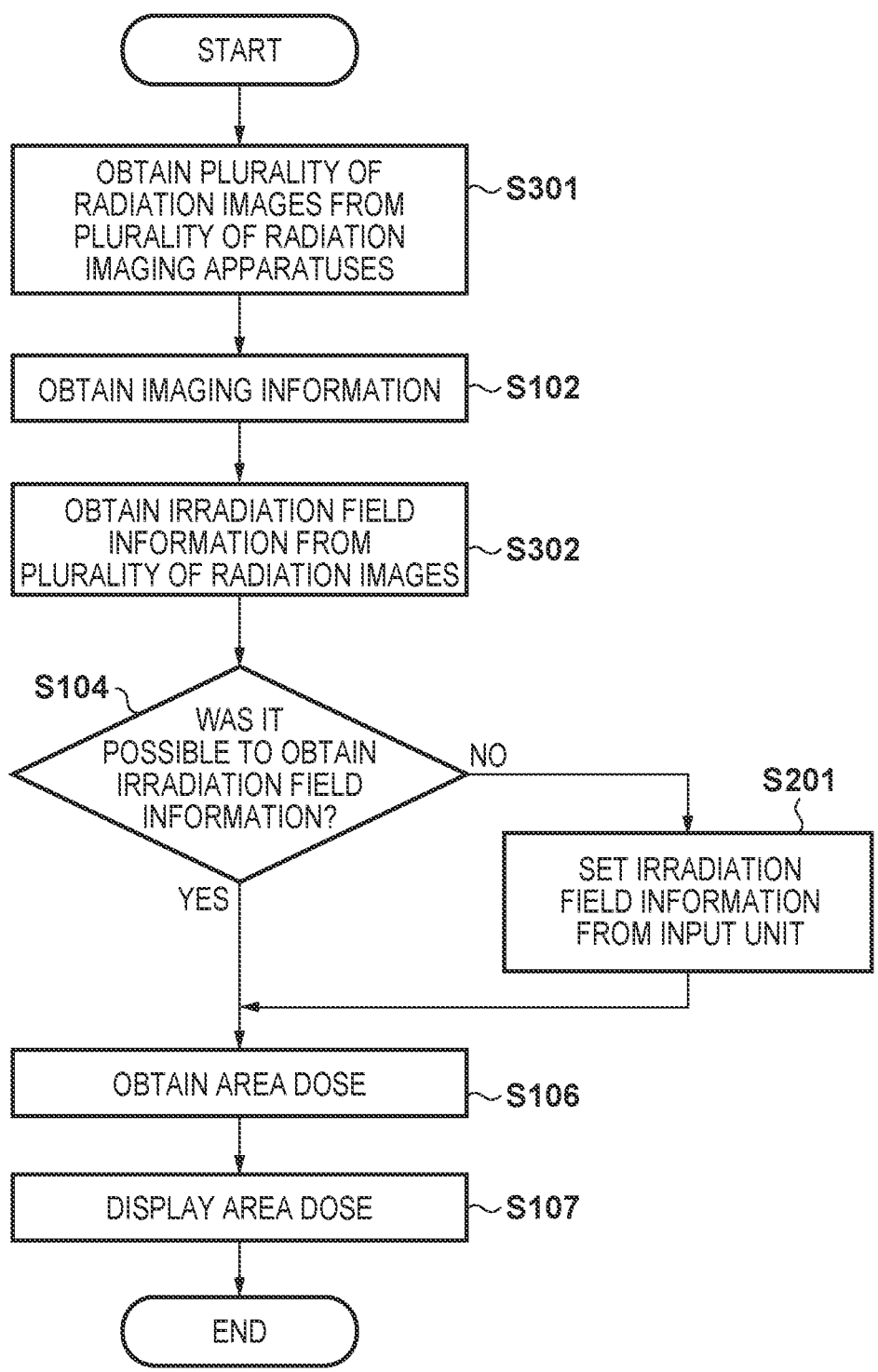
FIG. 12 is a flowchart for explaining a procedure for processing according to the third embodiment.

FIG. 12 explains a procedure for processing according to the third embodiment, and is a flowchart for explaining a procedure for the processing of obtaining an area dose and displaying the obtained area dose. The irradiation field obtaining unit 115 performs the processing of obtaining irradiation field information concerning a plurality of radiation images as the first irradiation field obtaining method (step S302). If no irradiation field information concerning any one of the plurality of radiation images can be obtained (NO in step S104), irradiation field information is obtained by the second irradiation field obtaining method different from the first irradiation field obtaining method (step S201).

FIG. 12 explains a case in which each of a plurality of radiation images is processed. However, it is also possible to process a long-length image obtained by combining a plurality of radiation images as one radiation image.

That is, the irradiation field obtaining unit 115 performs the processing of obtaining irradiation field information concerning a long-length image as the first irradiation field obtaining method (step S302). If no irradiation field information concerning the long-length image can be obtained (NO in step S104), it is also possible to obtain irradiation field information by the second irradiation field obtaining method different from the first irradiation field obtaining method (step S201).

A procedure in the flowchart of FIG. 12 will be described below. In step S301, the image obtaining unit 114 obtains a plurality of radiation images obtained by the plurality of radiation imaging apparatuses 103 and 301 by single irradiation with radiation from the radiation generating apparatus 102.

In step S102, an imaging information obtaining unit 113 obtains, as imaging information in radiation imaging, for example, a tube voltage, tube current, irradiation time, and mAs value from the radiation generating apparatus 102. In addition, the imaging information obtaining unit 113 obtains an SOD from information preset in the imaging control apparatus 101.

In step S302, the irradiation field obtaining unit 115 obtains an irradiation field in radiation imaging by applying the first irradiation field obtaining method to the plurality of obtained radiation images. In this embodiment as well, each of various methods can be used as the first irradiation field obtaining method.

As shown in, for example, FIG. 6, image processing can be used as the first irradiation field obtaining method (settings 601). Alternatively, irradiation field information can also be obtained based on the collimator information obtained from the radiation generating apparatus 102 (settings 602). In addition, it is also possible to use irradiation field information in which an irradiation field used for actual imaging before imaging is preset (settings 603).

Upon determining in step S104 that irradiation field information concerning a plurality of radiation images was able to be obtained by the previous processing in step S103 (YES in step S104), the irradiation field obtaining unit 115 advances the process to step S106. In contrast to this, upon determining in step S104 that no irradiation field information concerning at least any one of a plurality of radiation images can be obtained (NO in step S104), the irradiation field obtaining unit 115 advances the process to step S201.

Although the irradiation field obtaining unit 115 determines in step S104 whether irradiation field information concerning each of a plurality of radiation images was able to be obtained, the irradiation field obtaining unit 115 may also determine whether irradiation field information concerning a long-length image generated from a plurality of radiation images was able to be obtained.

In step S201, the irradiation field obtaining unit 115 sets irradiation field information input from an input unit 201 as the second irradiation field obtaining method. The irradiation field obtaining unit 115 can set irradiation field information based on the information input by the operator with the input unit 201.

In step S106, an area dose obtaining unit 116 obtains the area of an irradiation field based on the irradiation field information obtained in step S103 or S201. The area dose obtaining unit 116 then obtains an area dose based on the area of the irradiation field and the irradiation dose obtained by using the simplified dose obtaining method.

The area dose obtaining unit 116 obtains an area dose corresponding to a long-length image by totalizing a plurality of area doses obtained concerning a plurality of radiation images. If a long-length image is obtained by combining two radiation images, the area dose obtaining unit 116 totalizes two area doses corresponding to the two radiation images constituting the long-length image.

The area dose obtaining unit 116 can obtain the area of an irradiation field by excluding an overlapping portion due to the spatial arrangement of the plurality of radiation imaging apparatuses 103 and 301. The overlapping portion can be obtained based on positional information about the plurality of radiation imaging apparatuses 103 and 301.

In step S107, a display control unit 117 performs display control to cause the display unit to display the area dose obtained in step S106.

The flowchart of FIG. 12 exemplifies a case in which upon determining in step S104 that no irradiation field information can be obtained, the irradiation field obtaining unit 115 sets irradiation field information based on the information input from the input unit 201 as the second irradiation field obtaining method (step S201). However, another setting method can also be used as the second irradiation field obtaining method.

As described with reference to FIG. 2, it is also possible to use, as the second irradiation field obtaining method, irradiation field information in which an irradiation field used for actual imaging before imaging is preset (step S105).

As described with reference to FIG. 3, irradiation field information may be obtained based on collimator information from the radiation generating apparatus 102 as the second irradiation field obtaining method (step S108). Alternatively, as described with reference to FIG. 4, in a case no irradiation field information can be obtained by the first irradiation field obtaining method (step S103), it is also possible to perform display control to cause the display unit to perform display notification indicating that no area dose can be obtained (step S109).

As described with reference to FIG. 5, an irradiation field in radiation imaging can be obtained by applying the second irradiation field obtaining method (image processing based on another algorithm) to an obtained radiation image (step S110). If no irradiation field information can be obtained even by applying the second irradiation field obtaining method (image processing based on another algorithm) (NO in step S111), the irradiation field obtaining unit 115 can also set irradiation field information based on the information based on the processing in step S201 in FIG. 10, that is, the information input from the input unit 201, as the third irradiation field obtaining method (step S201).

According to this embodiment, it is possible to obtain an area dose based on irradiation field information in executed long-length imaging.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-093978, filed May 15, 2018, which is hereby incorporated by reference herein in its entirety.

What is claimed is:

1. An imaging control apparatus, comprising:
   an irradiation field obtaining unit configured to obtain irradiation field information in radiation imaging by an irradiation field obtaining method; and
   an area dose obtaining unit configured to obtain an area dose in the radiation imaging based on the irradiation field information, wherein
   when the irradiation field information is not obtained by a first irradiation field obtaining method, the irradiation field obtaining unit obtains the irradiation field information based on a second irradiation field obtaining method different from the first irradiation field obtaining method,
   the first irradiation field obtaining method being an irradiation field obtaining method based on at least one of a radiation image obtained by radiation imaging, imaging information associated with the radiation imaging, and preset irradiation field information concerning the radiation imaging, and
   the second irradiation field obtaining method being based on at least one of the radiation image obtained by radiation imaging, imaging information associated with the radiation imaging, and preset irradiation field information concerning the radiation imaging other than said first irradiation field obtaining method.

2. The apparatus according to claim 1, wherein the irradiation field obtaining unit performs image processing for the radiation image in the first irradiation field obtaining method, and obtains the irradiation field information based on information included in the imaging information in the second irradiation field obtaining method.

3. The apparatus according to claim 2, further comprising an input unit configured to input the irradiation field information, wherein
   when the irradiation field information is not obtained by the first irradiation field obtaining method or the second irradiation field obtaining method, the irradiation field obtaining unit obtains the input irradiation field information as irradiation field information in the radiation imaging.

4. The apparatus according to claim 1, wherein the irradiation field obtaining unit performs processing for obtaining the irradiation field information based on information included in the imaging information in the first irradiation field obtaining method, and obtains the irradiation field information based on image processing for the radiation image in the second irradiation field obtaining method.

5. The apparatus according to claim 1, wherein the irradiation field obtaining unit Obtains the irradiation field information based on collimator information concerning a radiation generating apparatus that is included in the imaging information.

6. The apparatus according to claim 1, wherein the irradiation field obtaining unit performs image processing for the radiation image in the first irradiation field obtaining method, and obtains irradiation field information in the radiation imaging based on irradiation field information preset as an imaging condition in radiation imaging in the second irradiation field obtaining method.

7. The apparatus according to claim 6, wherein when irradiation field information preset as information is included in an imaging condition for the radiation imaging, the irradiation field obtaining unit obtains the preset irradiation field information as irradiation field information in the radiation imaging.

8. The apparatus according to claim 7, wherein the irradiation field obtaining unit obtains the irradiation field information based on image processing for the radiation image or the preset irradiation field information in the second irradiation field obtaining method.

9. The apparatus according to claim 7, wherein the irradiation field obtaining unit obtains the irradiation field information based on image processing for the radiation image or information included in the imaging information in the second irradiation field obtaining method.

10. The apparatus according to claim 1, wherein the irradiation field obtaining unit performs processing of obtaining irradiation field information in the radiation imaging based on irradiation field information preset as an imaging condition in radiation imaging in the first irradiation field obtaining method, and obtains the irradiation field information based on image processing for the radiation image in the second irradiation field obtaining method.

11. The apparatus according to claim 1, further comprising a storage unit configured to store a dose information table associating the imaging information in the radiation imaging or a preset imaging condition for the radiation imaging with an irradiation dose in the radiation imaging, wherein
   the area dose obtaining unit obtains a corresponding irradiation dose from the dose information table based on the imaging information or the imaging condition, and obtains the area dose based on the obtained corresponding irradiation dose and an area of an irradiation field obtained from the irradiation field information.

12. The apparatus according to claim 11, wherein when a change in imaging condition is input from an input unit after radiation imaging, the area dose obtaining unit obtains the area dose based on an irradiation dose obtained from the dose information table based on the imaging condition after the change and an area of the irradiation field.

13. The apparatus according to claim 12, wherein the irradiation field obtaining unit obtains the irradiation field information by executing image processing using an imaging condition after a change.

14. The apparatus according to claim 1, further comprising an image obtaining unit configured to obtain a radiation image by radiation imaging based on radiation applied from a radiation generating apparatus, wherein
   the image obtaining unit obtains plural radiation images by plural radiation imaging apparatuses by single irradiation with radiation from the radiation generating apparatus, and the image obtaining unit generates a long-length image by using a plurality of the obtained radiation images.

15. The apparatus according to claim 14, wherein the irradiation field obtaining unit performs processing of obtaining the irradiation field information concerning the plurality of radiation images as the first irradiation field obtaining method, and obtains the irradiation field information by said second irradiation field obtaining method if irradiation field information concerning at least one of the plurality of radiation images is not obtained.

16. The apparatus according to claim 14, wherein the irradiation field obtaining unit performs processing of obtaining the irradiation field information concerning the long-length image as the first irradiation field obtaining method.

17. The apparatus according to claim 1, further comprising a display control unit configured to cause a display unit to display the area dose obtained by the area dose obtaining unit.

18. The apparatus according to claim 17, wherein when the irradiation field information is not obtained, the display control unit causes the display unit to display a notification indicating that the area dose is not obtained.

19. The apparatus according to claim 1, further comprising an imaging information obtaining unit configured to obtain imaging information in the radiation imaging from a radiation generating apparatus.

20. An imaging control apparatus, comprising:
an irradiation field obtaining unit configured to obtain irradiation field information in radiation imaging; and
an area dose obtaining unit configured to obtain an area dose in the radiation imaging based on the irradiation field information, wherein
the irradiation field obtaining unit performs image processing for the radiation image as a first irradiation field obtaining method, and obtains the irradiation field information by performing image processing different from an algorithm for the image processing as a second irradiation field obtaining method when the irradiation field information is not obtained by the first image processing, or
the first irradiation field obtaining method is an irradiation field obtaining method based on at least one of the radiation image obtained by radiation imaging, imaging information associated with the radiation imaging, and preset irradiation field information concerning the radiation imaging, and the second irradiation field obtaining method is an irradiation field obtaining method different from the first irradiation field obtaining method based on at least one of the radiation image obtained by radiation imaging, imaging information associated with the radiation imaging, and preset irradiation field information concerning the radiation imaging.

21. The apparatus according to claim 20, wherein image processing in the first irradiation field obtaining method is processing based on an algorithm corresponding to each imaging portion, and image processing in the second irradiation field obtaining method is processing based on an algorithm that is not limited by an imaging portion.

22. A radiation imaging system comprising a radiation imaging apparatus and an imaging control apparatus configured to control a radiation generating apparatus, the imaging control apparatus comprising:
an irradiation field obtaining unit configured to obtain irradiation field information in the radiation imaging by an irradiation field obtaining method; and
an area dose obtaining unit configured to obtain an area dose in the radiation imaging based on the irradiation field information, wherein
when the irradiation field information is not obtained, the irradiation field obtaining unit obtains the irradiation field information based on a second irradiation field obtaining method different from the first irradiation field obtaining method,
the first irradiation field obtaining method is an irradiation field obtaining method based on at least one of the radiation image obtained by radiation imaging, imaging information associated with the radiation imaging, and preset irradiation field information concerning the radiation imaging, and
the second irradiation field obtaining method is an irradiation field obtaining method based on at least one of the radiation image obtained by radiation imaging, imaging information associated with the radiation imaging, and preset irradiation field information concerning the radiation imaging other than the first irradiation field obtaining method.

23. An imaging control method for an imaging control apparatus, the method comprising the steps of:
obtaining irradiation field information in radiation imaging by an irradiation field obtaining method; and
obtaining an area dose in the radiation imaging based on the irradiation field information, wherein
when the irradiation field information is not obtained by a first irradiation field obtaining method, the irradiation field information is obtained based on a second irradiation field obtaining method different from the first irradiation field obtaining method,
the first irradiation field obtaining method is an irradiation field obtaining method based on at least one of the radiation image obtained by radiation imaging, imaging information associated with the radiation imaging, and preset irradiation field information concerning the radiation imaging, and
the second irradiation field obtaining method is an irradiation field obtaining method based on at least one of the radiation image obtained by radiation imaging, imaging information associated with the radiation imaging, and preset irradiation field information concerning the radiation imaging other than the first irradiation field obtaining method.

24. A non-transitory computer readable storage medium storing a program for causing a computer to execute each step in an imaging control method defined in claim 23.

25. An imaging control apparatus, comprising:
an irradiation field obtaining unit configured to obtain irradiation field information in radiation imaging by a first irradiation field obtaining method based on at least one information of a radiation image obtained by radiation imaging, imaging information associated with the radiation imaging, and preset irradiation field information concerning the radiation imaging, said irradiation field obtaining unit also being configured to obtain irradiation field information in radiation imaging by a second irradiation field obtaining method based on other information different from the first irradiation field obtaining method; and
an area dose obtaining unit configured to obtain an area dose in the radiation imaging based on the irradiation field information, wherein
when a first irradiation field information is obtained by the first irradiation field obtaining method, the irradiation field obtaining unit obtains the first irradiation field information based on the first irradiation field obtaining method, and when the first irradiation field information is not obtained by the first irradiation field obtaining method, the irradiation field obtaining unit obtains a second irradiation field information based on the second irradiation field obtaining method.

* * * * *